(12) United States Patent
Vander Jagt et al.

(10) Patent No.: US 6,888,633 B2
(45) Date of Patent: May 3, 2005

(54) COLOR MEASUREMENT INSTRUMENT WITH MODULATED ILLUMINATION

(75) Inventors: Peter G. Vander Jagt, Belmont, MI (US); Steven H. Peterson, Wyoming, MI (US)

(73) Assignee: X-Rite, Incorporated, Grandville, MI (US)

( * ) Notice: Subject to any disclaimer, the term of this patent is extended or adjusted under 35 U.S.C. 154(b) by 334 days.

(21) Appl. No.: 10/147,009

(22) Filed: May 16, 2002

(65) Prior Publication Data

US 2003/0048449 A1 Mar. 13, 2003

Related U.S. Application Data

(60) Provisional application No. 60/351,164, filed on Jan. 23, 2002, and provisional application No. 60/291,534, filed on May 16, 2001.

(51) Int. Cl.[7] ............................................... G01J 3/50
(52) U.S. Cl. ..................................... 356/407; 250/226
(58) Field of Search ............................... 356/406, 407, 356/405; 250/226

(56) References Cited

U.S. PATENT DOCUMENTS

| | | | |
|---|---|---|---|
| 3,994,590 A | 11/1976 | Di Martini et al. | |
| 5,995,858 A | 11/1999 | Kinast | |
| 6,006,119 A | * 12/1999 | Soller et al. | 600/322 |
| 6,206,830 B1 | 3/2001 | Diab et al. | |
| 6,583,880 B2 | * 6/2003 | Berstis | 356/407 |

FOREIGN PATENT DOCUMENTS

| DE | 3706056 | 5/1988 |
|---|---|---|
| FR | 2758389 | 7/1998 |

OTHER PUBLICATIONS

Balluff Inc., *Balluff BFS–26K Compact Color Sensors*, available at http://www.balluff.com/BFS/default.htm.

Vydas International Marketing, *Programmable Colour Sensors*, available at http://www.vydas.co.uk/prod21.htm (last modified Nov. 22, 2001).

Sensor Instruments GmbH, *Product Literature for SI–COLO Series Reflex Color Sensors*, Oct. 9, 2001.

Pepperl & Fuchs, *Product Literature for VCS 110 Series Color Sensors*, 2001.

Sensor Instruments GmbH, *Product Literature for SI–COLO Series Reflex Color Sensors*, Apr. 10, 2000.

SICK Optic Electronic, 2000 Photoelectrics Catalog, 576–581.

Mike Frey, *A Sense of the Future*, Industrial Computing, Oct. 1999 at 24.

OMRON Corporation, *Product Literature for RGB Color Sensor Model E3MC*, Oct. 1999.

Keyence Corporation, *Product Literature for RGB Digital Fiberoptic Sensor CZ Series*, 1999.

* cited by examiner

*Primary Examiner*—F. L. Evans
(74) *Attorney, Agent, or Firm*—Warner Norcross & Judd

(57) ABSTRACT

An instrument and method for measuring light or color using modulated illumination. The system includes an LED illuminator modulated at a specific frequency for illuminating the sample, and a sensor capable of differentiating between the modulated light from the sample and unmodulated ambient light. The instrument is therefore capable of "seeing" only light from the sample, while ignoring ambient light. In a second embodiment, the system includes multiple illuminators of different colors each modulated at a unique frequency so that the sample can be measured at multiple at each of the different frequencies.

28 Claims, 6 Drawing Sheets

COLOR MEASUREMENT INSTRUMENT WITH MODULATED ILLUMINATION

PRIORITY CLAIM

This application claims the benefit of U.S. Provisional Application No. 60/291,534 filed May 16, 2001 entitled "Modulating LEDs to Maintain Selectivity and Sensitivity in Density or Color Measuring Instrumentation" and U.S. Provisional Application No. 60/351,164 filed Jan. 23, 2002 entitled "Light or Color Measuring Instrumentation Based on Modulated LED Illumination."

BACKGROUND OF THE INVENTION

1. Field of the Invention

The present invention relates to color measurement instruments and, more specifically, to such instruments using light-emitting diodes (LEDs) as the illumination source.

2. Description of the Art

The ability to monitor and/or control color is beneficial in many areas of manufacturing. The performance requirements for measuring color from application to application differ greatly and the hardware solutions that result are perhaps as varied as the applications they serve. Nonetheless, a simple model can be posed where color measurement applications are to be thought of as falling somewhere along a simple linear Color Requirements Continuum (CRC) where the need for precision or accuracy is relatively high on one end and relatively low on the other end.

On the high end of the CRC are those processes where color is critical and must be scrutinized closely such as in printing, textiles, coatings, and film or digital image processing. In such applications, the colors to be measured or controlled are usually measured with precise instruments such as densitometers, spectrophotometers, or spectral radiometers. Such measurements may occur on-line or off-line, but in either case the instrumentation deployed tends to be precise, repeatable, and absolute rather than relative and specific to the application. Consequently such instrumentation is somewhat expensive.

On the low end of the CRC are those applications where some aspect of color is needed for a manufacturing process, but precision or absolute color is not a high requirement. These applications include such things as sorting items by color, or gauging some parameter of a process by color (e.g. watching for the crust to brown when baking bread). A variety of simple and robust RGB (Red, Green, Blue) color sensors generally serve this portion of the CRC. Such sensors usually differentiate color no finer than what could very easily be discerned by human vision in less than ideal lighting. The sensors are often used in situations where non-contact color measurement is required. These sensors tend to be more industrial in nature and often utilize an inexpensive PLC (Programmable Logic Controller) or RS-232 type of interface.

In the middle ground of the CRC, there is a demand for more precise color measurement, approaching the color discernment capabilities of instruments on the high end. Yet these applications cannot relax their requirement for environmental robustness, simplicity and reliability as demanded by industrial applications. Unfortunately, such applications often cannot fully justify the price of the industrially hardened high-end spectrophotometric solutions.

Existing approaches to low-cost industrial, sub-spectrophotometric color measurement fall into two general categories: (1) wide band illumination (i.e. white light) with the color differentiation occurring at the sensor, and (2) separate RGB illumination sources (to provide color differentiation) with detection performed by a simple wide band sensor. A common implementation of the first approach is exemplified by a pulsed xenon source and three filtered photodiodes. A common implementation of the second approach is exemplified by the Keyence technique of sequentially pulsing high brightness LEDs in red, green, and blue to illumine a sample that is then measured with a wide band sensor. Both of the above approaches seek to minimize the adverse affects of ambient lighting by using high levels of light at the instant of measurement or compensating for ambient light with differential measurements. The above techniques have served the low end of the CRC very well but continue to fall short of middle ground desires for precision, repeatability, or resolution in color discernment.

SUMMARY OF THE INVENTION

The aforementioned problems are overcome in the present invention in which a color measurement instrument uses a continuously modulated illuminator so that the detector can be tuned to the modulated reflected light and can ignore the unmodulated ambient light. The instrument modulates the illuminator (one or more outputs) at a specific carrier frequency and then uses narrow band filtering in the detector to see only light that is modulated at the specific frequency. Consequently, the instrument nullifies the effects of ambient light in a fashion that is relatively simple, efficient, and inexpensive.

In the preferred embodiment, the illuminator is one or more light-emitting diodes (LEDs), which are becoming increasingly effectively used for illumination. The light output of LEDs can be effectively modulated in ways that other light sources cannot. Using continuously modulated LED illumination is an innovative enhancement to the RGB LED illumination of the above noted prior art because it uses a single wide band sensor and relies on the pseudo-monochromatic nature of LED light to provide the needed spectral color differentiation. Additionally, the present invention may use more than the three RGB colors of the prior art. Though slightly more complex in design, the present invention provides several distinct advantages. Differentiation of the color signal from the color noise of ambient light is done almost entirely in a simple frequency domain rather than having to rely on spatial means (i.e. optical geometries) or time differential means (i.e. measurement of ambient with signal minus measurement of ambient without signal) to achieve good signal-to-noise ratios.

In a further preferred embodiment, the frequency-based isolation of the instrument's light source can be done simultaneously for each of the LED colors enabling fast and simultaneous acquisition of each component of the measured color.

The present invention results in several advantages. Using the LED modulation and detection techniques of the present invention enables the design of accurate, robust, and cost-effective solid-state color instrumentation providing performance and cost-effective coverage of the middle ground of the CRC. A light or color measuring instrument, based on LED modulation, is impervious to most forms of ambient light. This characteristic enables the instrument to target and view the sample of interest during the measurement. LED light sources have implicit size, power, spectral, and optical characteristics that can be exploited to minimize complexity and cost in a given instrument or application. The design of instruments based on LED modulation is not confined to a single LED channel or emission-wavelength range, but can be expanded to accommodate multiple LED channels (i.e. the whole visual spectrum) and the multi-channel solution can retain the sensitivity and selectivity advantages found in single channel implementations. The design of instruments based on LED modulation will increasingly benefit from improving LED efficiencies, spectral coverage, and the availability of high performance/resolution analog-to-digital (A/D) converters and Digital Signal Processors, which will perform the vast majority of the signal processing tasks required by this technology in the digital domain.

These and other objects, advantages, and features of the invention will be more readily understood and appreciated by reference to the detailed description of the preferred embodiment and the drawings.

DETAILED DESCRIPTION OF THE PREFERRED EMBODIMENTS

I. Background

Figure 1:
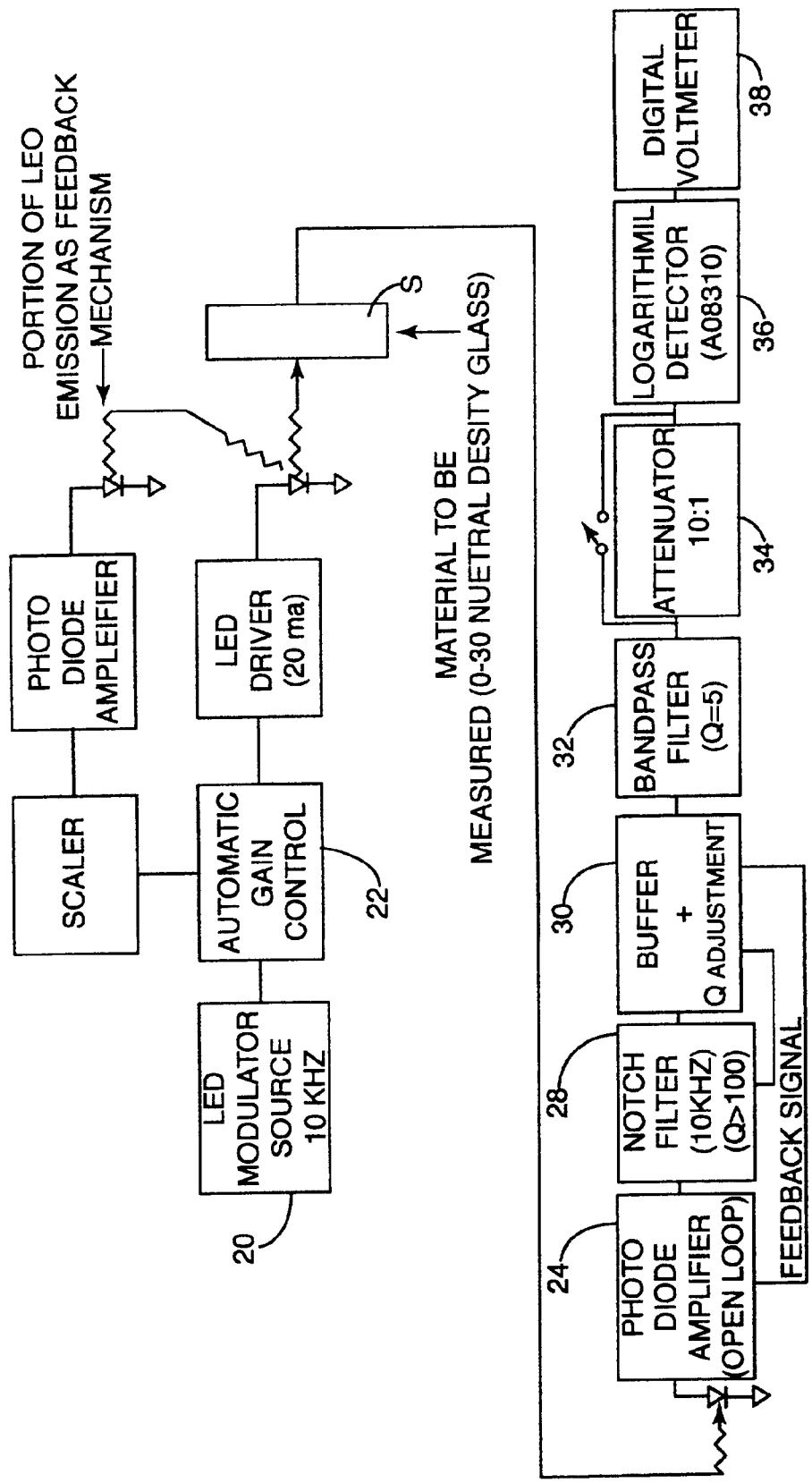
FIG. 1 is a block diagram of Experiment 1.

Light Emitting Diodes (LEDs) are rapidly becoming the preferred means of providing general purpose illumination. LEDs are small, inexpensive, low power, long lived semiconductor devices that, in modern times, are extremely bright and easy to use and, yet, have room for further optimization, particularly in the areas of packaging, spectral coverage, and efficiency. Because LEDs are semiconductor devices, their costs have decreased dramatically and predictably as automation and economies of scale have been applied in the fabrication process. Until recent times, LEDs could not generate the entire range of colors in the visual spectrum (i.e. blue-violet to deep red) because they were physically bound, in their emission characteristics, to the short list of materials from which they were made. But as more semiconductor materials have been discovered and manufacturing processes have evolved, along with organic substitutes (OLEDs) and phosphor supplementation (i.e. white LEDs), the gaps in LED spectral coverage have shrunk while the LEDs themselves have become much more efficient sources of light.

There are two particular aspects of LEDs that are useful when compared to incandescent lamps. The first is that, because LEDs emit light at specific wavelengths, they can be thought of as light sources with implicit and totally efficient optical filters. As LED manufacturing techniques have improved, LEDs have become available in wavelengths that were previously thought to be unattainable and manufacturers have also learned to tune LED chemistries for the customer's needs. Secondly, LEDs are current operated devices that respond to changes of input current nearly instantaneously. This means that the normal DC current required to power an LED can be modulated at extremely high frequencies (e.g. approximately 1 MHz). This capacity for high frequency modulation can be exploited to enhance two essential characteristics in light and color measuring instrumentation: selectivity and sensitivity.

With regard to selectivity, modulation frequency can be used to distinguish a given light source from ambient light conditions and the detector can be designed to reject the ambient condition. In other words, if a source of light, an LED, is being modulated at X frequency, then a detector can be designed to respond ONLY to X frequency and to no others. This means that a detector with a wide spectral range of sensitivity can be made to see and only see the modulated light source which, in the case of LEDs, can have relatively narrow spectral coverage. This property permits non-contact measurements (shoe-less is the term in the art) which are not affected by ambient light even if that ambient light (e.g. a laser) is actually generated by the measuring device to assist the operator in targeting the sample. This attribute of selectivity also allows the operator to actually see and position the sample while it is being measured, which, when combined with the ability to measure quickly, allows the operator to apply scientific intuition to the measurement process in real time. Wide spectral coverage is obtained by modulating several LEDs with different spectral emission characteristics in sequence and measuring the resultant output from the detector circuit. The detector will only be sensitive to the LED being modulated and, in that way, one sensor with wide spectral sensitivity can measure many channels of LED emission.

With regard to sensitivity, modulation restricts the signal of interest to one frequency. Detection/amplification techniques can take advantage of this property to maximize the signal to noise margin during the measurement. Detector and amplifier circuits that measure light that is not modulated are sensitive to signal processing artifacts such as voltage offsets, stray currents, thermal drift, and random and spurious forms of electronic noise that narrow band detection/amplification of an AC signal can filter, avoid, or submerge. Such artifacts limit the useful dynamic range of an instrument so that measurements of samples that transmit or reflect small amounts of light are not reliable or repeatable. Narrow band detection and amplification, of a frequency removed from typical noise sources, will improve the stability of light and color measurements and expand the dynamic range of instrumentation based on such measurements. Small modulated signals of interest can exist in noisy, ambient conditions that are hundreds or even thousands greater in magnitude and still be measured accurately. The primary limiting factor to the dynamic range of an instrument that incorporates narrow band amplification of the signal of interest will be the sensor or sensor amplifier's own noise floor in the frequency range of interest, not external sources of noise, provided that narrow band amplification occurs immediately in the signal processing chain at or near the detector. Dynamic range can be further expanded by incorporating a programmable gain amplifier (PGA) in the signal processing chain, following the detector/amplifier, to boost the signal of interest to levels that can be measured accurately by conventional A/D conversion technology.

II. Experiment 1

In Experiment 1, circuitry was developed to demonstrate the advantages of using a current modulated LED as a light source and combining that light source with frequency selective detection/amplification. The goal was to verify that modulated LED light could be measured in ambient light conditions with a dynamic range of three to four decades. FIG. 1 shows a block diagram of Experiment 1. The LED light source was a 520 nanometer (nm) green LED, which was chosen because its peak wavelength was close to the peak sensitivity of the human eye and because green LEDs represent the middle of the road in terms of LED efficiency (reds are more efficient while blues are less efficient). The LED was current modulated by making it, with a current limiting resistor, the load in a voltage controlled current sink (VCCS). The LED was operated at a nominal 20 milliamperes DC, which is the ideal operation point for most LEDs in a 5 mm. package. A 10 kHz sine wave modulator 20 was impressed upon the DC voltage that set the LED current. The resultant LED current, when monitored by the sense resistor of the VCCS circuit, was the same as the DC condition, when measured with a digital voltmeter. But when viewed with an oscilloscope, the LED current was modulated to approximately 80% of the DC current value, which kept waveform distortion to a minimum.

There are two ways to close the loop around the light source in order to minimize modulator distortion and drift. The first is to close the loop right at the VCCS by using an LED Servo. AN LED Servo is an electronic circuit that accurately converts input control voltage to output light intensity. AN LED Servo implicitly corrects the non-linear relationship between drive current to an LED and light emitted from an LED by sensing a portion of the light emitted from an LED with a photodiode and by converting photodiode current to feedback voltage which, in turn, controls LED drive current. The use of an LED Servo to modulate and drive an LED device precludes the use of any other means of emission intensity compensation. The second way to close the loop around the light source is to use automatic gain control (AGC) 22 on the modulated portion of the light generated by the LED, which is a more flexible arrangement. The AGC circuitry 22 allows measurements to be made without worrying about drift in either the modulation source 20 or in the efficiency of the light source.

The detector used was a silicon photodiode assembly that included a modest IR filter to reject infrared light. It was discovered that bombarding the silicon photodiode with infrared light (i.e. from a high output incandescent light source at point blank range) disturbs the gain of the detector circuit at the modulation frequency. This effect is due to the inability of the detector/amplifier circuit to linearly respond and reject the photocurrents generated by illuminating the photo sensor with extremely high amounts of incident infrared (IR) or near infrared (NIR) light. The use of an optical filter, which begins to attenuate signals in the near-infrared (700 nm.), sufficiently suppresses this phenomenon so that bombardment with incandescent light does not interfere measurements of a modulated light source in the visible spectrum.

The principal quality of any circuit designed to exploit and measure modulated light is incorporating the vast majority of filtering in the first stage, the photodiode detector/amplifier stage, to preserve dynamic range. The photodiode detector/amplifier circuit used a composite (i.e. two stage) trans-impedance amplifier (TIA) 24 that incorporated two operational amplifiers (feedback from the second stage to the first) in the position where there is normally a single stage TIA. A TIA is an amplifier circuit that transforms the output of a current source (e.g. a photodiode) to a proportional voltage so that it can be measured or processed with traditional electronic techniques. In a preferred embodiment, the circuit is designed to respond only to a range of frequencies and to be sensitive to extremely small currents (i.e. pico-amps). A TIA is also referred to as a detector/amplifier.

Between the two amplifiers there is a passive/active network, commonly known a Twin-T notch filter 28, which was chosen because it has few parts and an extremely high and adjustable Q. Because the notch filter 28 is inside the feedback loop and because the gain resistor is set to the smallest value possible to retain stability, the first stage or sensor amplifier output is negligible at every frequency except where the notch filter 28 is tuned. The insertion loss of the notch filter 28, because it is within the feedback loop, forces the first stage to amplify the notch frequency at a gain equal to the notch filter attenuation. This design requires that the first stage has typical TIA attributes (i.e. low bias current, low offset, low noise) along with high gain-bandwidth product. The second stage amplifier also needs to have high gain-bandwidth product, but with the exception of low voltage noise, the other requirements are relaxed. A third amplifier 30 was added to adjust the Q of the notch filter 28, but an optimized design probably would eliminate this amplifier. The composite TIA design allowed instrumentation, based on a modulated LED light source, to be impervious to ambient light conditions—even ambient light conditions that are extreme except in the narrow band of interest—because the gain for all signals was near zero, With the setting of Q in this stage, there is a tradeoff between output level and pass band stability. The notch filter 28 can theoretically have infinite Q, but maximizing Q would make setting the modulation frequency (which must match the notch filter peak) incredibly difficult. In Experiment 1, the Q of the notch filter 28 was reduced to permit a modest amount of frequency drift in the signal generator, and a supplemental amplifier-filter stage was added for additional rejection of common noise sources (e.g. 60 Hz lighting). This additional stage is commonly known as a multiple feedback bandpass filter 32. The output from the multiple feedback bandpass filter 32 was coupled through an attenuator 34 to a logarithmic detector 36 (AC volts in/DC (decibel) output) to allow the conversion of transmitted light to a logarithmic scale (i.e. optical density) for the experiment. The dynamic range of the logarithmic detector was increased as needed by bypassing the attenuator 34.

The logarithmic detector 36 is a very convenient and practical way to convert AC signals to a DC output that can be directly measured with an analog to digital converter. The logarithmic detector 36 had a range of 4 decades in the amplitude domain (which can be expanded using prudent gain-switching techniques) and 400 MHz in the frequency domain, and it minimized the dynamic range requirements of the A/D converter that would normally follow the logarithmic detector 36 in the signal processing chain. In Experiment 1, it was convenient to determine the scale of the logarithmic detector 36 (nominally 24 millivolts/dB) using known calibrated glass neutral density filters. Once zero point was set and the scale of the logarithmic detector was known, density measurements were reduced to a simple calculation: Density of sample=[Voltage (no sample)−Voltage (with sample)]/Voltage to density (db) scale.

Tuning and calibration functions were performed manually. Practical implementations of the concept in instrumentation would either provide for continuous tuning of the LED modulation frequency to match the fixed notch filter location or of the notch filter location to match a fixed LED modulation frequency. In either case, the continuous tuning process would be momentarily interrupted when the need to perform a measurement was detected or a measurement was otherwise initiated. This technique would ensure that any drift mechanisms would not affect the dynamic range of the instrument, and would remove the need to perform some forms of calibration.

To check the circuitry for the ability to reject ambient light conditions, sources such as high output flashlights, DC operated LEDs, laser pointers etc. were directed towards the photodiode sensor or towards the material being measured S in an effort to disturb the output of the logarithmic amplifier 36 as measured by a DC responding digital voltmeter 38. None of these sources disturbed the measurement of the finalized circuitry, though the laser pointer and flashlight had many times the radiant flux of our modulated LED source.

Then the experimental circuitry, which as described is essentially performing the function of a transmission densitometer, was compared to other transmission densitometers. Transmission densitometry was the simplest instrumentation to model experimentally and the most demanding in terms of dynamic range. In addition to the neutral density glass filters, twenty-one step film strips or wedges were used for checking the measurement capability of the described circuitry. Once RF noise issues in the logarithmic detector 36 and stray light paths were addressed, measurements were very stable, even at high densities. Later tests, with the logarithmic amplifier circuitry optimized, proved that the linearity extended to 3 decades (3D) with remarkable conformance to proven instrumentation, which uses a two point calibration to enhance its accuracy at 3D. See the table below for a comparison of measurements of the experimental circuitry and the X-Rite Model 301. Because of the stability of the measurements, a significant portion of the small differences between the measurements are probably due to differences in geometry and calibration, rather than any inherent limitation in the circuitry or implementation of the circuitry.

Experiment 1 Data:

| Step (Nominal Density) | X-Rite Model 301 | Modulated LED |
|---|---|---|
| 0.1 | .09 | .09 |
| 0.3 | .25 | .29 |
| 0.5 | .47 | .49 |
| 1.0 | .93 | 1.02 |
| 2.0 | 1.87 | 1.87 |
| 3.0 | 2.90 | 2.88 |

III. Concept Development

Experiment 1 proved that LED modulation could be used to gain sensitivity in instrumentation scenarios that require a great deal of dynamic range while retaining spectral sensitivity to specific wavelengths of light and to provide these attributes in a somewhat hostile environment. But practical implementations of this technology require multi-channel measurements, where as few as three or as many as sixteen or more wavelengths of light are being measured simultaneously. This requirement represents a significant leap in terms of implementing modulated LED technology because the electronic circuitry becomes much more complex as the channel count increases. There are at least four approaches that extend the modulated LED technology into the multi-channel domain.

The first and simplest approach is to incorporate a number of LEDs at specific wavelengths and to modulate each of these LED channels in sequence. The advantage of this approach is that it results in the simplest analog circuitry and promises measurements that are accurate, stable, and consistent from channel to channel, an ideal circumstance for ratiometric measurements. The disadvantage is that sequential modulation of many LEDs implies long measurement times—equal, at best, to the number of channels times the base measurement time. This problem can be addressed by raising the modulation frequency to a maximal position, and this becomes extremely important when resolving signals buried in noise since, in an optimized system, measurement accuracy is gained at the expense of time. LEDs can be modulated at frequencies approaching 1 MHz, so reasonable performance can be obtained in a sequential design. But higher frequencies demand more expensive components, and inevitably the brick wall of photodiode capacitance will be encountered in the detector/amplifier circuitry. Another disadvantage for some applications is that sequential measurements are inherently non-synchronous, which may prevent the system from working when the sample is a fast moving web or part on the assembly line.

A second approach is a parallel implementation of the original concept starting at the detector sensor. For example, in the case of a four channel implementation, this approach modulates four LEDs at distinct frequencies and measures with four individual detector/amplifier circuits that share a prepackaged array of four individual photodiodes in close proximity to each other (i.e. a quadrant-type photodiode). The advantage of this approach is that parallelism allows synchronous measurements and electronic tuning of each LED channel. The disadvantage is that parallelism requires a very complex and expensive implementation of the original circuitry equal to approximately the number of electronic components in the original design times the number of LED channels. Another disadvantage is that parallel multi-channel implementations have channel cross-talk issues that must be addressed in design. In practice, cross-talk can be minimized by augmenting the detector/amplifier circuitry with appropriate forms of filtering or by using electronic correlation techniques.

A third approach is to combine the sequential and parallel approaches so that the system, though not optimal purely from the standpoint of capability or circuitry, is satisfactory for the application at hand. In other words, by combining the ability to perform sequential measurements of LED channels with a prescribed amount of parallelism, the total LED channel counts obtained are considerably higher than would be economically feasible with a fully parallel implementation and considerably faster, in terms of measurement time, than a fully sequential implementation. The number of LED channels that can be addressed in this way is the product of the number of parallel channels in the implementation times the number of sequential measurements made in each channel. For example, if a 16 channel system is required and the circuitry or power requirements are not to significantly exceed that found in an exclusively parallel four channel system, then each of the four parallel channels could be expanded using sequential techniques (i.e. multiplex 4 individual LEDs on each of the 4 parallel channels; 4 parallel channels×4 multiplexed LEDs=16 LED channels). This approach places no greater requirement of channel discrimination than the second approach, and measurement time would be approximately one fourth of a sixteen channel implementation based on the first approach.

An alternative to the first three brute force approaches is a fourth approach, which replaces the narrow-band detector/amplifier design of the previous approaches with a wide-band detector/amplifier circuit that uses synchronous demodulation or Fourier transformation to create a number of extremely narrow-band filters, one for each unique modulation source or LED channel. As in the first approach, one detector/amplifier circuit is shared by all LED channels. But unlike the first approach, each LED channel is modulated by a unique but similar frequency. The output of the detector/amplifier will be a composite signal. A composite signal is a complex electronic signal that represents the sum of the light emitted from the LED devices (i.e. LED channels) and reflected back from the target to the detector. Because this signal contains many similar and high frequencies, it requires the detector to be capable of high frequency operation and wide dynamic range. If the composite signal can be demodulated (i.e. separated again to constituent LED channels), then the magnitude of those channels represents light or color information about the sample.

As in the second approach, there is parallelism in that each LED channel has a unique modulator (or frequency) and demodulator thereby allowing for synchronous measurements. As in the third approach, there are application specific derivatives of this approach that can incorporate various amounts of parallelism according to a given measurement requirement or cost constraint. This approach, then, embodies many of the positive attributes of the first three approaches, but there are also disadvantages. One disadvantage to this approach is that it will compromise the ambient light and noise rejection of the detector/amplifier circuit, a primary attribute of the first three approaches. However, this compromise can be quite modest if the band of interest is high enough in frequency since most ambient light sources are either low frequency (e.g. 120 Hz incandescent lighting) or low amplitude (e.g. fluorescent lighting). Another disadvantage is that a constituent part of synchronous demodulation is a final stage low pass filter (or a time consuming computation in the case of a Fourier transformation), which will compromise measurement speed. But there are ways to minimize the measurement speed penalty. Another disadvantage with this approach is that any parallelism is implicitly complex and expensive because this approach requires components that can be expensive. This can also be addressed. The advantage of this approach is that it fits the "measurement based on modulated LED illumination" scenario so well. For one thing, the modulation frequency and phase for each LED channel is known or can be ascertained during the calibration phase of operation, which means that—even with analog-to-digital (A/D) latencies—synchronous demodulation can be employed. Secondly, synchronous demodulation, being phase sensitive, allows one to measure frequencies of interest that reside coincidentally with Guassian noise of the same frequency. Thirdly and in response to the above disadvantages, much of the parallelism and complexity implicit in this approach in terms of electronic hardware can be eliminated and the performance can be optimized by processing signals in the digital domain with a suitable digital signal processor (DSP).

Because of the implicitly longer measurement times and non-synchronous behavior of sequential approaches (i.e. the first approach), some parallelism is probably required in a practical implementation of this modulated LED technology for many markets. However, approaches that rely entirely on parallelism (i.e. the second approach) are too complex and expensive, particularly if they are implemented in the analog domain. Hybrid combinations (i.e. the third approach) are feasible, even if the implementation is confined to the analog domain, but they will always be application specific, which is a considerable limitation if cost reduction is a priority. Therefore, the approach with the most potential for optimization and cost reduction is the fourth approach, named Modulated LED Spectral Assessment (MLSA).

Figure 2:
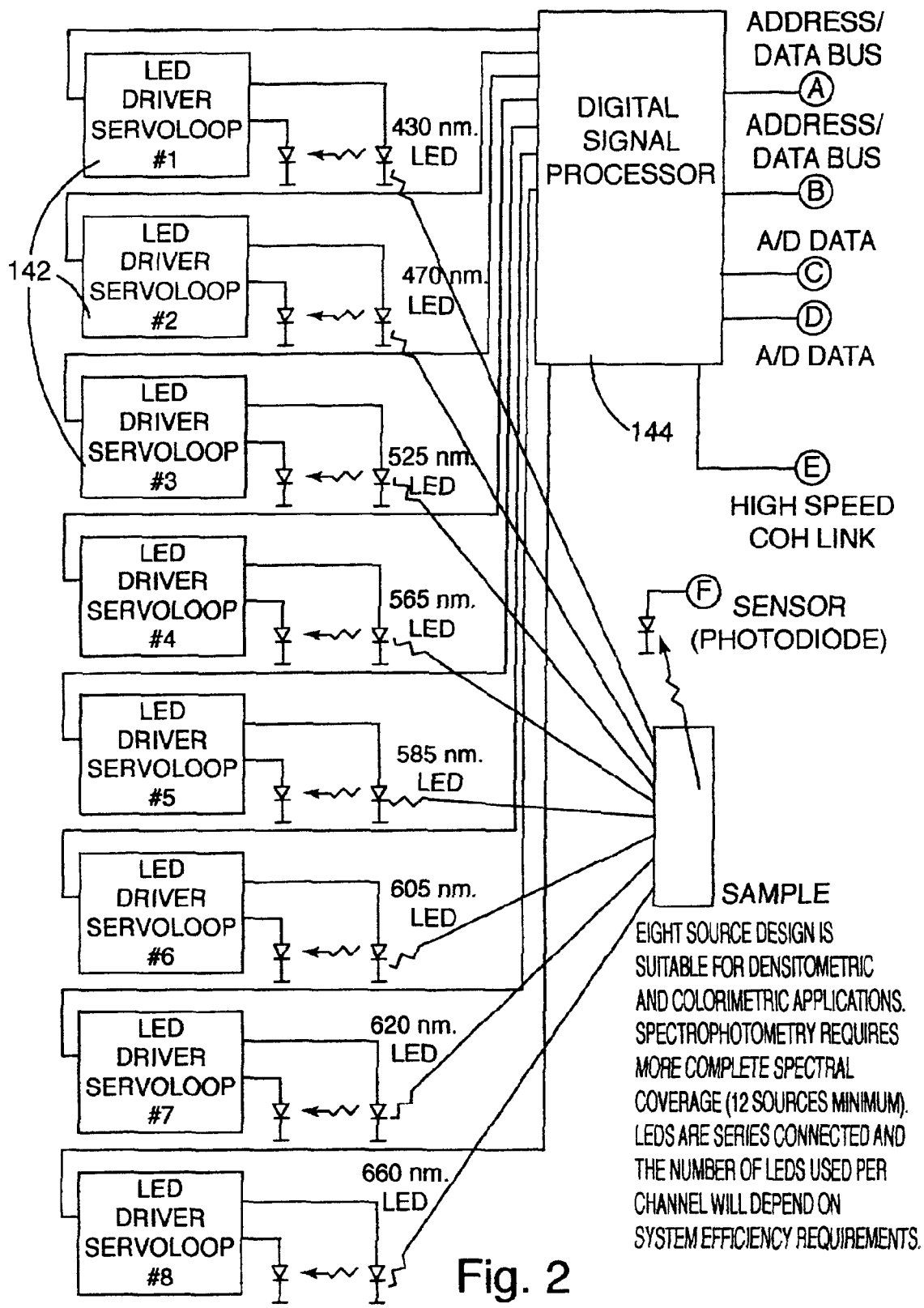
FIG. 2 is a block diagram of a modulated LED spectral assessment design.
Figure 3:
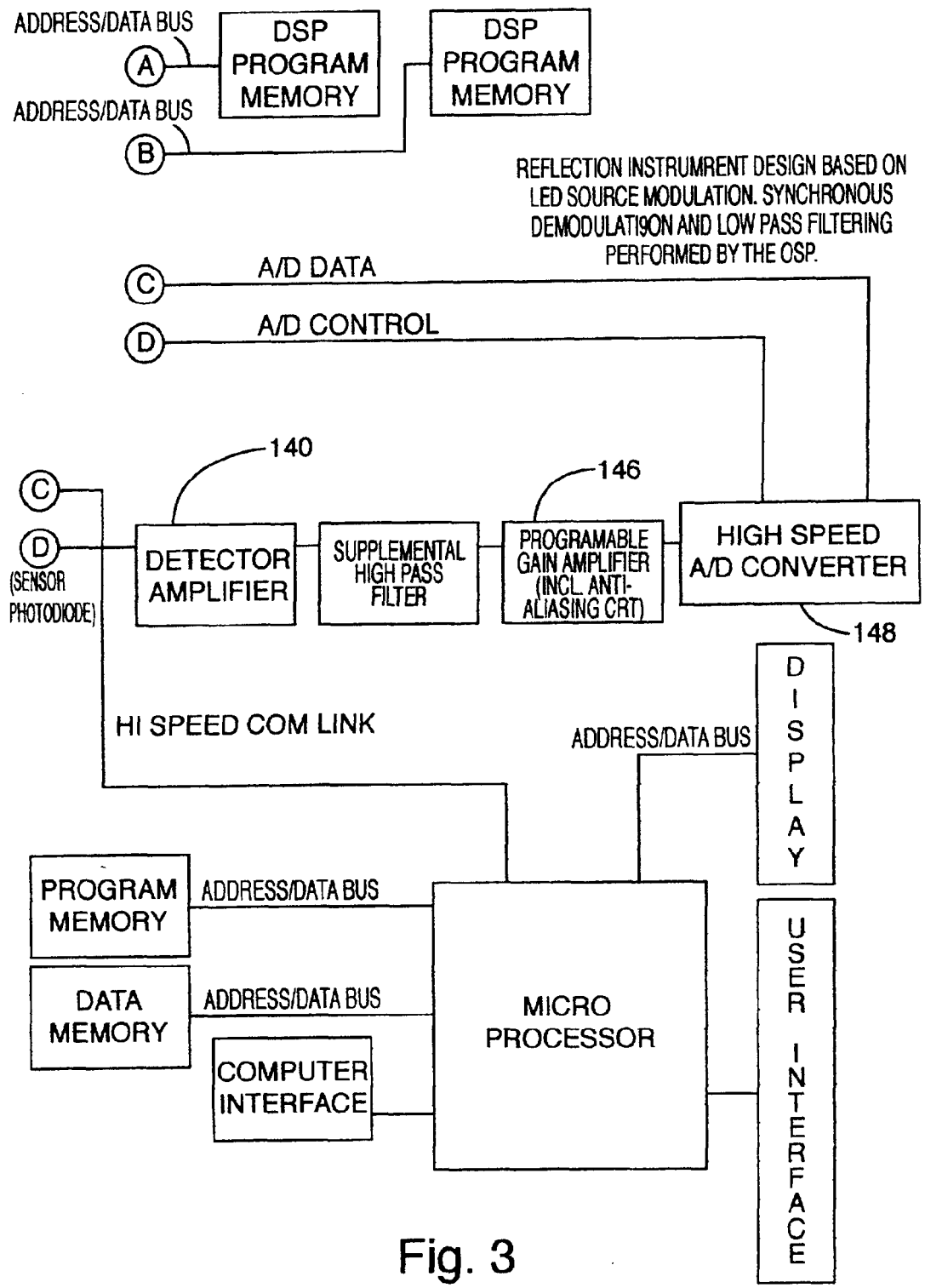
FIG. 3 is a continuation of FIG. 3.

MLSA is a measurement technique that uses the emission characteristics and modulation capabilities of LED devices to perform spectral measurements of reflective or transmissive samples. MLSA is reasonably fast, synchronous, and, because of the inclusion of synchronous demodulation, has extremely wide dynamic range capability. Much of the complexity of MLSA can be moved to the digital domain so that a production implementation of the approach would not be expensive or complex, and much of the capability of MLSA can be modeled simply and rapidly in the analog domain. FIGS. 2–3 show a block diagram of a MLSA design.

MLSA is challenging to implement, particularly in areas where analog circuitry cannot be replaced by a digital equivalent. Two areas of concern are the detector/amplifier stage and the LED Modulation sources. With regard to the detector/amplifier stage, MLSA requires the design of the detector/amplifier 140 to be wide band in the frequency domain instead of the narrow band design as used in Experiment 1. This wide band detector/amplifier 140 must be capable of passing, without attenuation or appreciable phase shift, multiple LED modulation frequencies or channels while rejecting the DC and low frequency AC energy that is commonly found in ambient lighting. Because of this change in the original detector/amplifier design, the original two stage TIA was replaced with a single stage TIA designed to perform significantly faster and quieter than typical single stage TIA implementations. For one thing, the TIA must have greatly improved gain-bandwidth characteristics so that gain or phase shift can be minimized in the frequency range of interest (e.g. 80 kHz to 1 MHz). This requires, in turn, that the effects of photodiode capacitance must be minimized. The detector/amplifier band pass roll-off requirement, on the high side, can be satisfied by the high frequency limitations of the photodiode capacitance and TIA. However, as in the narrow band design, a great deal of low frequency filtering must occur in the TIA if low level signals of interest are to be measured in the presence of high amounts of ambient light.

With regard to the LED modulation sources, they are ideally simple, inexpensive, stable, and easily controlled. The waveforms generated by the sources would, ideally, have no harmonic content (i.e. sine waves), which would allow the maximum number of LED channels for a given range of frequencies. But high quality sine wave generators with these attributes are difficult to design in the analog domain and expensive in the digital domain. However, if the range of modulation frequencies can be limited so that they reside between the fundamental (i.e. the lowest frequency LED channel) and the third harmonic of the fundamental, then alternate waveforms can be considered, such as triangle and square waves, but the use of these alternate waveforms requires a careful examination of bandwidth in the signal processing chain so that the presence of higher order harmonics does not compromise the demodulation function. Triangle waves, despite their low harmonic content, are almost as difficult to create and control as sine waves and were not seriously considered, although their use in conjunction with logarithmic amplifiers does present some intriguing possibilities for extremely wide dynamic range measurements. The final alternative is to modulate LED devices with a square wave generator. Square waves are simple to generate, extremely stable, and easily controlled. In fact, a microprocessor, DSP 144, or programmable logic device can generate many highly accurate, phase related, square waves using internal counter/timer facilities. The square waves can then be easily modified by passing them through filter networks to limit the higher order harmonics, thus reducing slew rate requirements of the signal processing chain. Stability remains an issue, even when the waveform generator is stable, because the emission characteristics of LEDs are not.

A useful method to maintain consistent emissions from LED modulation sources is to enclose the LED driver inside an LED Servo 142. LED Servo circuits 142 force the LED emission to be proportional to the signal input at the LED Servo. This means that one can assume the LED emission is constant, which makes measurements non-ratiometric. Without the use of LED Servo circuits 142 for each LED modulation source, there will need to be either a common monitor of LED emission whose signal processing chain mirrors the functionality of the sample light path (starting with the detector/amplifier and ending with the microprocessor or DSP, the measurement is now ratiometric) or a highly accurate characterization of LED drift over time and temperature. LED Intensity Characterization (LEDIC) is an analysis of characteristic LED emission in the magnitude domain, which results in a means for compensating LED emission drift and non-linearity. The means is a look-up table that includes and accounts for variables such as initial brightness, ambient temperature, chip temperature, operating current, and hours of use. LEDIC is required when compensation for changes in illuminator emissions must be approximated. LED Color Characterization (LEDCC) is an analysis of characteristic LED emission in the spectral (color) domain, which results in a means for compensating LED spectral drift. The means is a look-up table that includes and accounts for variables such as initial center wavelength, ambient temperature, chip temperature, operating current, and hours of use. LEDCC is required when compensation for changes in the spectral qualities of an LED must be approximated.

An instrument design using MLSA would have a programmable gain amplifier (PGA) 146 that has at least one decade (preferably two) of gain adjustment after the detector/amplifier. The PGA 146 can be constructed with analog circuitry or, in some cases, it is a feature of an A/D converter 148. Following the PGA 146, the demodulation process can occur. Demodulation separates the individual LED modulation frequencies or channels so their amplitude can be measured. Synchronous demodulation is a preferred means of demodulation, but Fourier transformation of the composite signal is also effective. Synchronous demodulation requires a perfect knowledge of the LED modulation frequency and phase as inputs and this is not exactly straightforward because of phase shifts in circuitry and A/D conversion processes, but having these inputs, synchronous demodulation essentially creates extremely narrow band, phase sensitive filters that, theoretically, can separate the closely spaced LED modulation frequencies.

IV. Experiment 2

Figure 4:
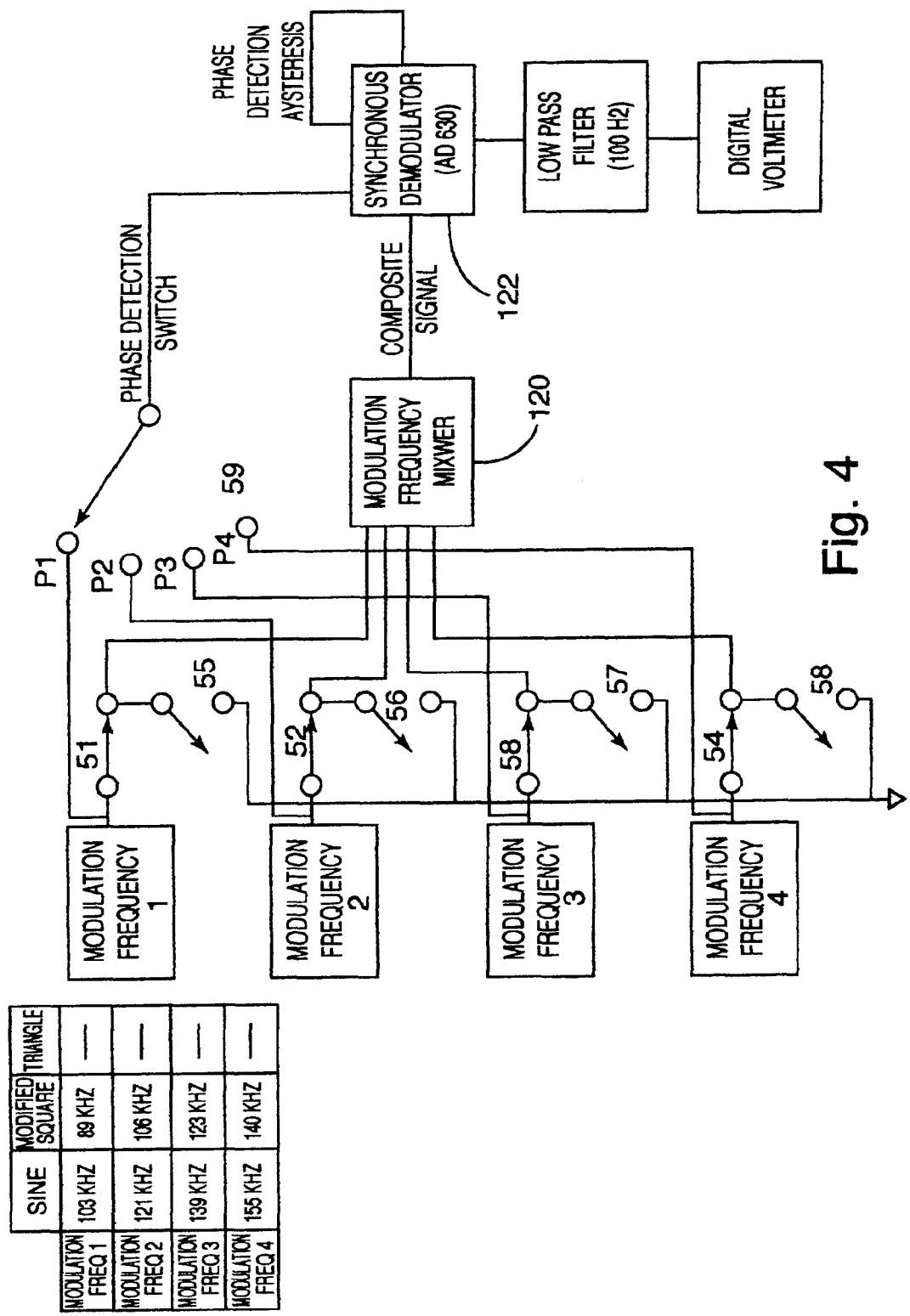
FIG. 4 is a block diagram of Experiment 2.
Figure 5:
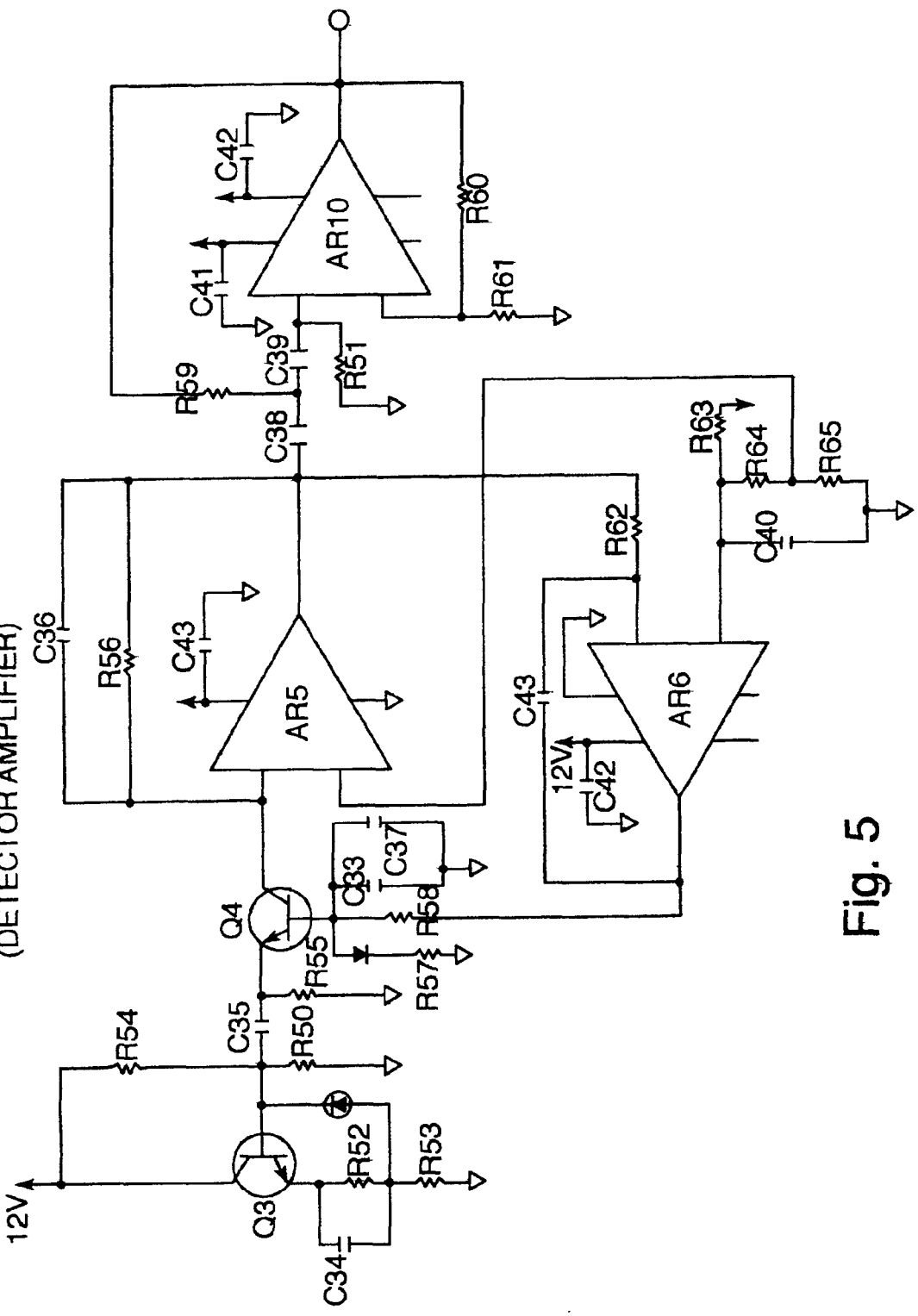
FIG. 5 is a schematic diagram of a detector/amplifier circuit.

Experiment 2 tested the various components of a MLSA design. FIG. 4 shows a block diagram of Experiment 2. The first step was to design an LED servo that is simple, stable, and accurate at 100 KHz and a high speed photodiode detector/amplifier circuit. FIG. 5 shows a schematic of experimental circuits. Designing the detector/amplifier circuitry was challenging because of the effect of photodiode capacitance, which must be minimized if frequency response is to be maximized. The best or most cost-effective solution appeared to be a combination of a number of techniques such as reverse biasing the photodiode to reduce photodiode capacitance, bootstrapping the photodiode to reduce the effect of photodiode capacitance, selecting an optimal operational amplifier with reduced capacitance at the amplifier inputs, and incorporating a cascode (common base transistor) amplifier between the photodiode and trans-impedance amplifier to swamp out the photodiode capacitance. Combining these techniques allowed the use of a commercially available blue-enhanced photodiode as the sensor in the detector/amplifier circuit.

Figure 6:
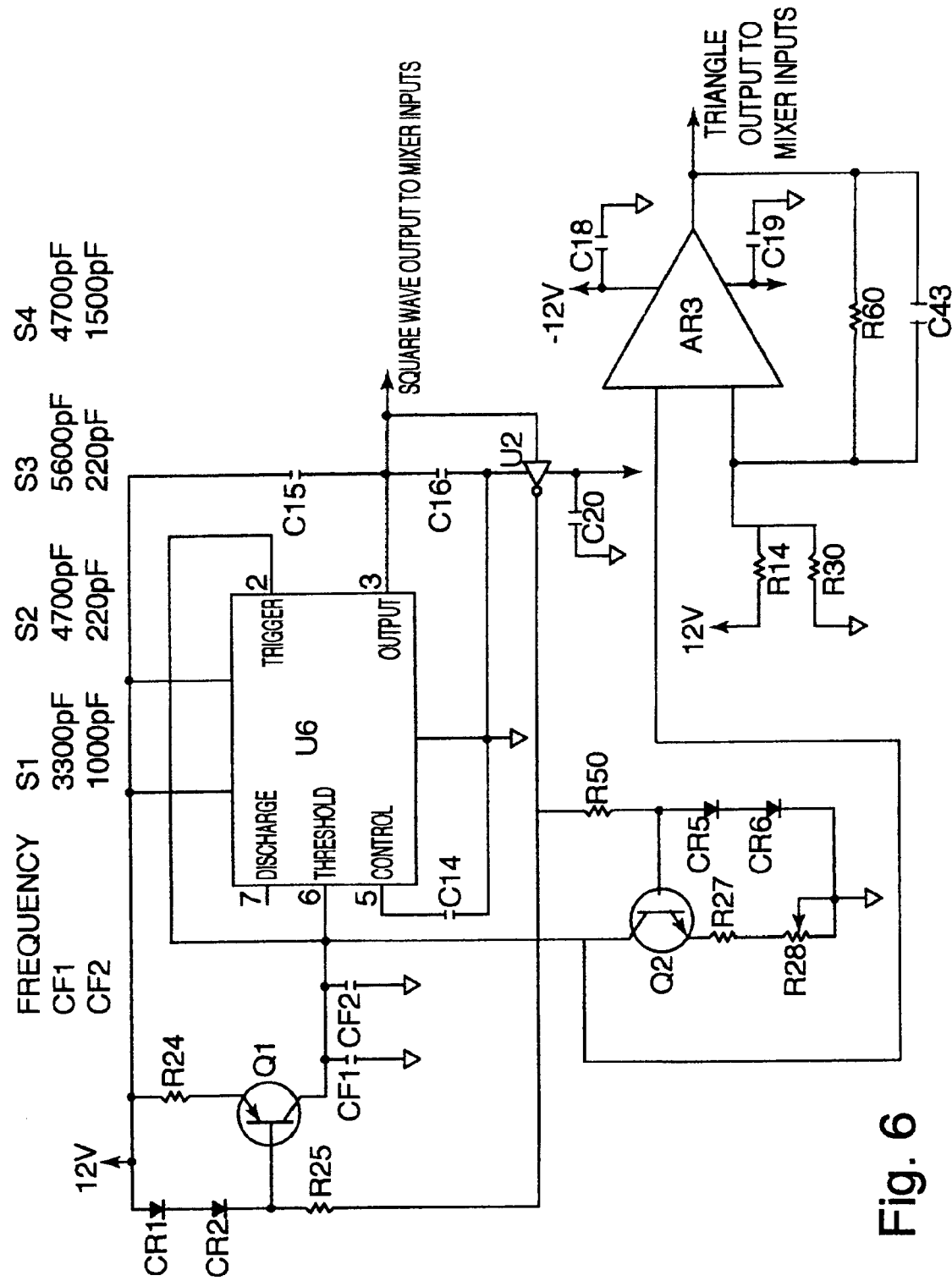
FIG. 6 is a schematic diagram of sine and modified square wave modulation sources.

Secondly, knowing that MLSA demands the ability to recover a number of LED modulation frequencies or channels from a composite signal, a mixer circuit 120 was designated that would emulate an actual detector/amplifier composite signal output of four independent (in frequency and phase) LED modulation sources. Sine and modified square wave modulation sources were designed at frequencies ranging from 90–140 kHz. FIG. 6 shows schematics of sine and modified square wave modulation sources. The goal of this experiment was to mix the four modulation frequencies or various combinations together in the mixer 120 and to un-mix these frequencies (represented as DC signals) using a synchronous demodulator 122. The experimental circuitry allowed the mixing of any combination of the four frequencies, although in collecting data on the demodulator's performance, it was deemed sufficient to test for cross-channel bleed using a mixture of three frequencies (i.e. fundamental plus any two of the remaining three channels) and to test with just one frequency (i.e. fundamental or any of the three off channels).

Source/Record Alignment Calibration (SRAC) is a method of discovering the time or phase relationship between the stimulus to an LED channel and the effect of that stimulus as recorded in the data record. This relationship is calculated by determining the zero crossing points of the calibration data record with only one LED channel active and turning those points until the synchronous demodulation calculation yields the maximum output in the LED channel of interest and the minimum output in the inactive channels. SRAC is repeated for all LED channels and is performed once or occasionally and the result is stored and applied to subsequent measurements.

Bleed/Offset Calibration (BOC) is a method of discovering and compensating for the effect of cross-channel bleed due to the presence of one frequency or LED channel while another frequency or LED channel, the channel of interest, is being measured. BOC occurs during the calibration process after SRAC and involves the creation of a lookup table that contains offsets which are scaled and subtracted from the signal measured in the channel of interest to improve the accuracy of the measurement. The dynamic range and separation capabilities were measured for two waveforms of interest, namely sine and modified square waves, of this basic implementation of synchronous demodulation.

Source/frequency selection calibration is a method of discovering and compensating for the effects of ambient lighting that exists in the modulation frequency range. LED modulation frequencies are selected to not be coincident or harmonically related to frequencies present in ambient light.

The data for Experiment 2 is shown below. There was little difference between the performance of the synchronous demodulator 122 using sine wave modulation and the performance of the same circuit using modified square wave modulation once the mixer circuit 120 was optimized by incorporating C13 to limit frequency response. Some shifts in the respective DC levels, that represent the modulation sources, were noted for various forms of kinds of mixing, but given the nature of the signals of interest (i.e. high frequency) and the circuit implementation (e.g. a hand-wired prototype), the results were good. For instrumentation purposes, Experiment 2 proved that the advantages of modulating many LEDs simultaneously and demodulating the resultant signals (as modified by sample reflectance or transmittance) using synchronous demodulation far outweigh the disadvantages (i.e. circuit cost, complexity, and peculiar noise considerations) which makes the technology defined as MLSA an appropriate and effective method to approach color measurements.

Definitions:

| Sine | Modified Square |
|---|---|
| Frequency 1 (F1): 103 Khz | 89 Khz |
| Frequency 2 (F2): 121 Khz | 106 Khz |
| Frequency 3 (F3): 138 Khz | 123 Khz |
| Frequency 4 (F4): 155 Khz | 140 Khz |
| Switch 1 (S1) enables F1 to Mixer | |
| Switch 2 (S2) enables F2 to Mixer | |
| Switch 3 (S3) enables F3 to Mixer | |
| Switch 4 (S4) enables F4 to Mixer | |
| All ON equates to S1–S4 switches ON | |
| All OFF equates to S1–S4 switches OFF | |
| Phase 1 (S9-P1)-Demodulator Phase Input Channel is F1 | |
| Phase 2 (S9-P2)-Demodulator Phase Input Channel is F2 | |
| Phase 3 (S9-P3)-Demodulator Phase Input Channel is F3 | |
| Phase 4 (S9-P4)-Demodulator Phase Input Channel is F4 | |

Data for Sine Wave Demodulation Test

| F1 Active: | Voltage (D.C.) |
|---|---|
| All ON | 1.0893 |
| S2 OFF | 1.0942 |
| S3 OFF | 1.0952 |
| S4 OFF | 1.1122 |
| All OFF | .0001 |

This is a cross-channel bleed test of the demodulator output when monitoring Frequency 1 (103 kHz) for combinations of Frequencies 1–4 mixed together. All ON is all frequencies present in the composite signal. S2 OFF is all ON except Frequency 2, etc. All numbers relate to Frequency 1. Note small shifts with various frequencies active. All OFF shows demodulator output with Frequency 1 used as the phase gate but no frequency present in the composite signal (input).

| F1 Only: | Voltage(D.C.) |
|---|---|
| P1 | 1.1132 |
| P2 | .0014 |

| | |
|---|---|
| P3 | .0021 |
| P4 | .0013 |

This is an offset test showing the amount of signal that results from operating the synchronous demodulator with the four different phase gate inputs. If only Frequency 1 is connected to the "mixer" (S1 ON, S2–4 OFF), how much signal is measured at the demodulator output when Frequency 1 is used as the demodulator phase gate (P1). What about Frequency 2 (P2), etc.?

| F2 Active: | Voltage (D.C.) |
|---|---|
| All ON | 1.1103 |
| S1 OFF | 1.1145 |
| S3 OFF | 1.1150 |
| S4 OFF | 1.1120 |

This is a cross-channel bleed test of the demodulator output when monitoring Frequency 2 (121 kHz) for combinations of Frequencies 1–4 mixed together. All ON is all frequencies present in the composite signal. S1 OFF is all ON except Frequency 1, etc. All numbers relate to Frequency 2. Note small shifts with various frquencies active.

| F2 Only: | Voltage (D.C.) |
|---|---|
| P1 | .0012 |
| P2 | 1.1316 |
| P3 | .0025 |
| P4 | .0063 |

This is an offset test showing the amount of signal that results from operating the synchronous demodulator with the four different phase gate inputs. If only Frequency 2 is connected to the "mixer" (S2 ON, S1, S3, S4 OFF), how much signal is measured at the demodulator output when Frequency 2 is used as the demodulator phase gate (P2). What about Frequency 1 (P1), etc.?

| F3 Active: | Voltage (D.C.) |
|---|---|
| All ON | 1.1430 |
| S1 OFF | 1.1453 |
| S2 OFF | 1.1431 |
| S4 OFF | 1.1580 |

This is a cross-channel bleed test of the demodulator output when monitoring Frequency 3 (138 kHz) for combinations of Frequencies 1–4 mixed together. All ON is all frequencies present in the composite signal. S1 OFF is all ON except Frequency 1, etc. All numbers relate to Frequency 3. Note small shifts with various frequencies active.

| F3 Only: | Voltage (D.C.) |
|---|---|
| P1 | .0014 |
| P2 | .0030 |
| P3 | 1.1583 |
| P4 | .0189 |

This is an offset test showing the amount of signal that results from operating the synchronous demodulator with the four different phase gate inputs. If only Frequency 3 is connected to the "mixer" (S3 ON, S1, S2, S4 OFF), how much signal is measured at the demodulator output when Frequency 3 is used as the demodulator phase gate (P3). What about Frequency 1 (P1), etc.?

| F4 Active: | Voltage (D.C.) |
|---|---|
| All ON | .9861 |
| S1 OFF | .9860 |
| S2 OFF | .9718 |
| S3 OFF | .9731 |

This is a cross-channel bleed test of the demodulator output when monitoring Frequency 4 (155 khz) for combinations of Frequencies 1–4 mixed together. All ON is all frequencies present in the composite signal. S1 OFF is all ON except Frequency 1, etc. All numbers relate to Frequency 4. Note small shifts with various frequencies active.

| F4 Only: | Voltage (D.C.) |
|---|---|
| P1 | .0028 |
| P2 | .0061 |
| P3 | .0086 |
| P4 | .9797 |

This is an offset test showing the amount of signal that results from operating the synchronous demodulator with the four different phase gate inputs. If only Frequency 4 is connected to the "mixer" (S4 ON, S1, S2, S3 OFF), how much signal is measured at the demodulator output when Frequency 4 is used as the demodulator phase gate (P4). What about Frequency 1 (P1), etc.?

| Data for Modified Square Wave Demodulation Test | |
|---|---|
| F1 Active: | Voltage (D.C.) |
| All ON | 3.143 |
| S2 OFF | 3.133 |
| S3 OFF | 3.134 |
| S4 OFF | 3.136 |
| All OFF | .004 |

This is a cross-channel bleed test of the demodulator output when monitoring Frequency 1 (89 khz) for combinations of Frequencies 1–4 mixed together. All ON is all frequencies present in the composite signal. S2 OFF is all ON except Frequency 2, etc. All numbers relate to Frequency 1. Note small shifts with various frequencies active. All OFF shows demodulator output with Frequency 1 used as the phase gate but no frequency present in the composite signal (input).

| F1 Only: | Voltage (D.C.) |
|---|---|
| P1 | 3.107 |
| P2 | .004 |
| P3 | .000 |
| P4 | −.002 |

This is an offset test showing the amount of signal that results from operating the synchronous demodulator with the four different phase gate inputs. If only Frequency 1 is connected to the "mixer" (S1 ON, S2–4 OFF), how much signal is measured at the demodulator -continued output when Frequency 1 is used as the demodulator phase gate (P1). What about Frequency 2 (P2), etc.?

| F2 Active: | Voltage (D.C.) |
|---|---|
| All ON | 3.065 |
| S1 OFF | 3.050 |
| S3 OFF | 3.054 |
| S4 OFF | 3.051 |

This is a cross-channel bleed test of the demodulator output when monitoring Frequency 2 (106 kHz) for combinations of Frequencies 1–4 mixed together. All ON is all frequencies present in the composite signal. S1 OFF is all ON except Frequency 1, etc. All numbers relate to Frequency 2. Note small shifts with various frequencies active.

| F2 Only: | Voltage (D.C.) |
|---|---|
| P1 | .003 |
| P2 | 3.013 |
| P3 | .004 |
| P4 | .002 |

This is an offset test showing the amount of signal that results from operating the synchronous demodulator with the four different phase gate inputs. If only Frequency 2 is connected to the "mixer" (S2 ON, S1, S3, S4 OFF), how much signal is measured at the demodulator output when Frequency 2 is used as the demodulator phase gate (P2). What about Frequency 1 (P1), etc.?

| F3 Active: | Voltage (D.C.) |
|---|---|
| All ON | 3.018 |
| S1 OFF | 2.998 |
| S2 OFF | 3.002 |
| S4 OFF | 3.004 |

This is a cross-channel bleed test of the demodulator output when monitoring Frequency 3 (123 kHz) for combinations of Frequencies 1–4 mixed together. All ON is all frequencies present in the composite signal. S1 OFF is all ON except Frequency 1, etc. All numbers relate to Frequency 3. Note small shifts with various frequencies active.

| F3 Only: | Voltage (D.C.) |
|---|---|
| P1 | .003 |
| P2 | .004 |
| P3 | 2.958 |
| P4 | .004 |

This is an offset test showing the amount of signal that results from operating the synchronous demodulator with the four different phase gate inputs. If only Frequency 3 is connected to the "mixer" (S3 ON, S1, S2, S4 OFF), how much signal is measured at the demodulator output when Frequency 3 is used as the demodulator phase gate (P3). What about Frequency 1 (P1), etc.?

| F4 Active: | Voltage (D.C.) |
|---|---|
| All ON | 2.949 |
| S1 OFF | 2.930 |
| S2 OFF | 2.926 |
| S3 OFF | 2.932 |

This is a cross-channel bleed test of the demodulator output when monitoring Frequency (140 kHz) for combinations of Frequencies 1–4 mixed together. All ON is all frequencies present in the composite signal. S1 OFF is all ON except Frequency 1, etc. All numbers relate to Frequency 4. Note small shifts with various frequencies active.

| F4 Only: | Voltage (D.C.) |
|---|---|
| P1 | .001 |
| P2 | .005 |
| P3 | .003 |
| P4 | 2.874 |

This is an offset test showing the amount of signal that results from operating the synchronous demodulator with the four different phase gate inputs. If only Frequency 4 is connected to the "mixer" (S4 ON, S1, S2, S3 OFF), how much signal is measured at the demodulator output when Frequency 4 is used as the demodulator phase gate (P4). What about Frequency 1 (P1), etc.?

V. Refinements

Synchronous demodulation can be accomplished using analog circuitry, but it is probably best accomplished in the digital domain using a high speed A/D converter (with provisions for PGA and anti-aliasing), which is controlled by a DSP. The DSP will function both as the modulation frequency generator or controller for the LED channels and the synchronous demodulator of the detector/amplifier output (as modified by the PGA, anti-aliasing filter etc.) and will allow the movement of most of the critical signal processing into the digital domain such as the synchronous demodulation and any other additional filtering that may be necessary to minimize cross-talk and remove noise. DSP operation involves converting and storing a fixed number of A/D conversion samples of the composite signal output of the PGA in to a data record in memory. Then the record is recursively analyzed for each constituent modulation frequency to derive the measurement data that corresponds to each LED channel. This process is called Recursive Synchronous Demodulation (RSD). RSD is a method of identifying and quantifying each frequency or LED channel in a digitally recorded composite signal and contains many unique frequencies. This method allows each frequency or LED channel to be accurately measured in the presence or absence of all other frequencies or LED channels. Because RSD uses the same record to measure all the frequencies or LED channels, the measurement can be said to be truly synchronous (i.e. simultaneous for all LED channels). RSD also allows for post-processing of many data records subsequent to a sequence of measurements that occur in burst fashion or a division-of-labor between a computing device that controls the measurement process and a computing device that processes the data record.

RSD is made possible by SRAC, which is used to determine the effective phase gate for each modulation frequency. As each LED channel is processed, compensations will be made for offset and cross-channel bleed effects using data gathered during BOC to yield the most accurate representation of sample reflectance or transmittance at a given wavelength. Because the same record is used to recover all the constituent LED channel values, the measurement is truly synchronous. If the A/D converter and DSP are sufficiently capable, then the band pass of LED modulation frequencies can be optimized, which appears to be between 50 and 150 kHz for the fundamental (i.e. lowest frequency) LED channel. At such frequencies, measurement times can be reasonably short (e.g. 0.01 to 0.001 seconds) for production line purposes.

The DSP could also be used to perform a Fast Fourier Transform (FFT) to identify the constituent modulation frequency (LED channels) and to measure each LED channel amplitude. Synchronous demodulation is probably a more appropriate technique, but regardless of which of the DSP signal processing technique is used, the accuracy of MLSA will be satisfactory because of the advantage of moving most of the signal processing to the digital domain.

One of the principal features of MLSA is that it allows the user or operator of an instrument, based on this technology, to view the sample as it is being measured. This feature would permit traditional optical instruments, such as colorimeters, densitometers, and spectrophotometers, to be used in non-typical environments such as agricultural measurements of plants (onsite, in daylight), or in miniaturized chemical laboratories to quickly determine the presence or absence of chemical compounds in soil or liquids (e.g. onsite environmental, chemical, or forensic studies) or in continuous duty monitoring of the optical transmission characteristics of liquids (e.g. onsite environmental or oceanographic studies). LEDs are not as power hungry or as thermally problematic as other illumination sources so traditional instrumentation designs based on this technology can be optimized in terms of size and hardened for use outside the laboratory.

The advantages of LED illumination and the techniques of LED modulation are not confined to traditional sciences. Rather, this technology could potentially usher in new families of user-friendly instruments to science, industry, and for consumers where, in the past, such instruments were thought to be too fragile, power-hungry, or expensive. These new instruments will exploit the advantages of LED illumination (i.e. long life, low power, high reliability, and low cost) and will provide them to buyers and users who will not require the extensive training implicit in the tradition color measuring sciences to perform simple, intuitive, non-contact color measurements for their own particular needs. For example, color measuring instruments based on this technology would be useful in any process requiring non-contact color measurement from considerable distances and in high ambient light conditions, which is the typical scenario for on-line inspection of packages, food, and automotive components. Furthermore, such a color measuring instrument, because of the properties of LEDs, would require little maintenance. Other potential applications of non-traditional instrumentation based on this technology can be found at the retail or consumer levels allowing the users or owners to measure and identify, in their own terms or in industry standard terms, the color of hair, skin, teeth, clothing, furniture, carpeting, paint, and other articles where maintaining cosmetic or aesthetic quality and uniformity are important.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. A method for measuring optical properties of a sample comprising:
    illuminating the sample including driving a plurality of light sources each having a unique spectral energy distribution and each modulated at a continuous frequency, said illuminating step further including providing servo control of each light source;
    detecting composite light including modulated sample light reflected by the sample from the modulated light sources; and
    filtering the composite light to separate the sample light at each of the continuous modulated frequencies from the composite light.

2. The method of claim 1 wherein the light sources are LEDs.

3. The method of claim 1 wherein said filtering step includes filtering out infrared light.

4. The method of claim 1 wherein each of the continuous frequencies is unique.

5. The method of claim 1 wherein each of the continuous frequencies is fixed.

6. The method of claim 5 wherein each of the fixed continuous frequencies is a sine wave, a triangle wave, or a square wave.

7. The method of claim 1 wherein said filtering step includes performing synchronous demodulation.

8. A method for measuring optical properties of a sample comprising:
    illuminating the sample including driving a plurality of illumitlators outputting different colors each at a continuous modulated frequency, said illuminating step further including providing closed loop control of the driving step to compensate for nonlinearity of the illuminators;
    detecting composite light including modulated sample light reflected by the sample from the illuminators; and
    filtering the composite light including filtering at each continuous modulated frequency to discriminate between sample light and other light within the composite light.

9. The method of claim 8 wherein each modulated frequency is unique.

10. The method of claim 8 wherein said filtering step includes using a single wide-band sensor.

11. The method of claim 8 wherein each modulated frequency is one of a sine wave, a triangle wave, or a square-wave.

12. The method of claim 8 wherein said filtering step includes performing synchronous demodulation.

13. The method of claim 8 wherein said filtering step includes performing a Fourier transformation.

14. The method of claim 9 wherein each unique continuous frequency is fixed.

15. An instrument for measuring optical properties of a sample comprising:
    illumination means for illuminating the sample, said illumination means including a plurality of spectrally unique light sources each modulated at a continuous frequency, said illumination means further including servo means for providing servo control for each of said light sources;
    detector means for detecting composite light including light of interest reflected by the sample from said illuminators, the composite light also including light not of interest reflected by the sample from other light sources; and
    filter means for filtering the composite light to separate the light of interest at each frequency from the light not of interest.

16. The instrument of claim 15 wherein said light sources each include an LED.

17. The instrument of claim 15 wherein each of said continuous frequencies is-a fixed frequency.

18. The instrument of claim 15 wherein said filtering means includes an infrared filter.

19. The instrument of claim 15 wherein each continuous frequency is unique.

20. The instrument of claim 15 wherein each continuous frequency is one of a sine wave, a triangle wave, or a square wave.

21. The instrument of claim 15 wherein said filter means includes means for performing synchronous demodulation.

22. An instrument for measuring optical properties of a sample comprising:
- illumination means for illuminating the sample with a plurality of light colors each modulated at a continuous frequency, said illumination means including illuminator for each of the light colors, said illumination means further including control means for providing closed loop control of said illuminators to compensate for the nonlinearity of said illuminators;
- detector means for detecting composite light including (a) sample light of interest reflected by the sample from said illumination means and (b) sample light not of interest reflected by the sample from other light sources; and
- filtering means for filtering the composite light at the continuous frequency of each light color to separate the sample light of interest from the sample light not of interest.

23. The instrument of claim 22 wherein each frequency is unique.

24. The instrument of claim 22 wherein said filtering means includes a single wide-band sensor.

25. The instrument of claim 22 wherein each continuous frequency is one of a sine wave, a triangle wave, or a square wave.

26. The instrument of claim 22 wherein said filtering means includes means for performing a synchronous demodulation.

27. The instrument of claim 22 wherein said filtering means includes means for performing a Fourier transformation.

28. The instrument of claim 22 wherein each continuous frequency is fixed.

* * * * *